United States Patent [19]

Brimmer et al.

[11] 4,106,620
[45] Aug. 15, 1978

[54] SURGICAL BLADE DISPENSER

[76] Inventors: Frances M. Brimmer, 3431 E. Monte Vista, Tucson, Ariz. 85717; Edward W. Ahrens, 4681 E. 32nd St., Tucson, Ariz. 85711; Herbert C. Magney, 433 W. Linda La., Chandler, Ariz. 85224

[21] Appl. No.: 838,589

[22] Filed: Oct. 3, 1977

[51] Int. Cl.² .......................................... B65D 83/10
[52] U.S. Cl. ................................. 206/363; 206/356; 206/359; 30/40.2
[58] Field of Search ............... 206/349, 356, 359, 363, 206/370; 30/40, 40.2, 123, 339

[56] References Cited

U.S. PATENT DOCUMENTS

| 2,562,513 | 7/1951 | Shnitzler | 206/356 |
| 3,002,607 | 10/1961 | Laverty | 206/228 |
| 3,172,316 | 3/1965 | Grieshaber | 30/339 |
| 3,728,788 | 4/1973 | Pearson | 30/40.2 |
| 3,760,938 | 9/1973 | Ferrier, Jr. | 206/356 |
| 3,833,146 | 9/1974 | Braginetz | 206/356 |
| 3,835,532 | 9/1974 | Petrillo | 30/40.2 |

FOREIGN PATENT DOCUMENTS 2,414,241  9/1975  Fed. Rep. of Germany ........... 206/359

Primary Examiner—William Price
Assistant Examiner—Bruce H. Bernstein
Attorney, Agent, or Firm—Drummond and Nelson

[57] ABSTRACT

A surgical blade dispenser includes a box for storing blades in such position that a scalpel handle can be inserted through an aperture in one wall of the box to lockingly engage one blade and remove it from the box through the aperture. The blades are individually positioned and supported within the box such that apertures in the shank portion of the blade are engagable with a mating boss on the forward end of the scalpel handle as the handle is inserted through an aperture in the wall of the box. Further insertion of the handle causes the boss to fully engage the aperture in the scalpel blade and, once complete engagement has been attained, the blade is withdrawn from the box by withdrawal of the handle through the aperture.

A blade disposal section is preferably included in the box. The handle aperture of the blade disposal section is provided with a metal edge. When a scalpel handle with a blade mounted thereon is inserted through the aperture, the rear edge of the blade can be engaged with the metal edge of the aperture and withdrawal of the handle strips the blade from the engaging boss, leaving the blade within the disposal section as the handle is withdrawn through the aperture.

2 Claims, 15 Drawing Figures

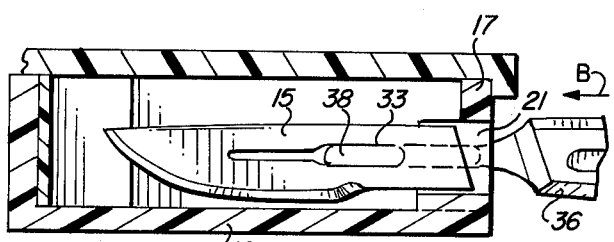
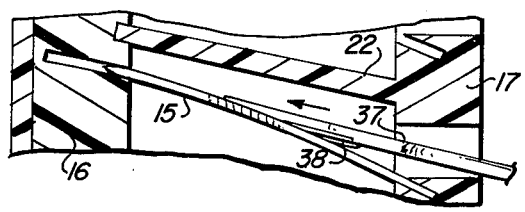
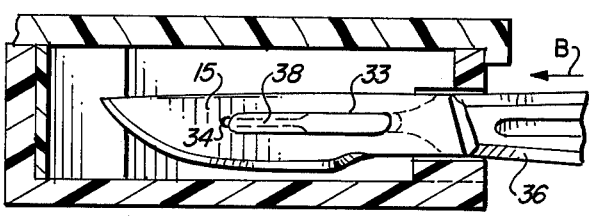
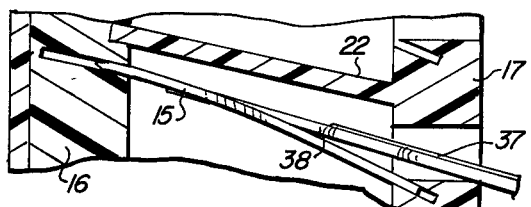
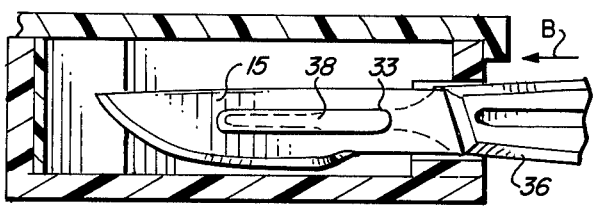
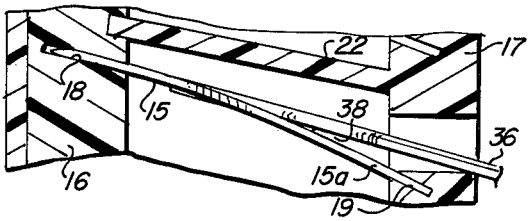
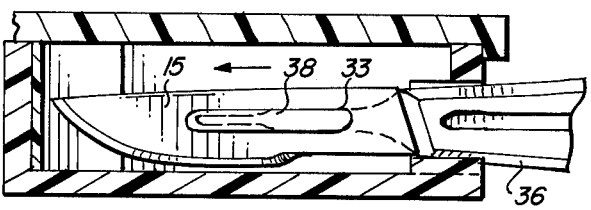
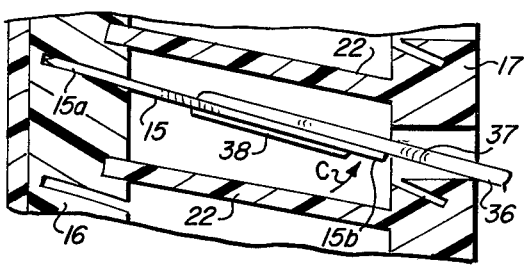
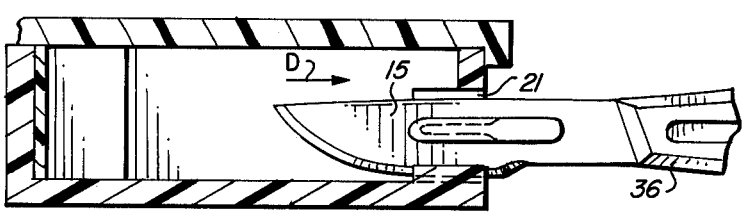
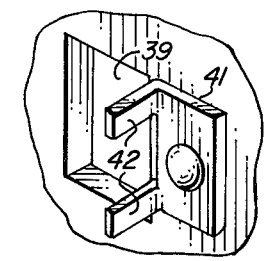
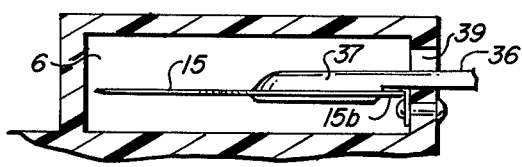
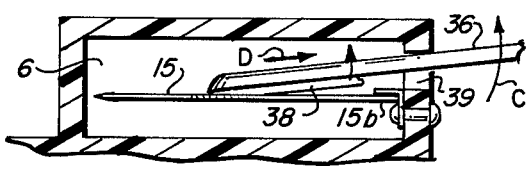

SURGICAL BLADE DISPENSER

This invention relates to dispensers for surgical blades.

In another respect, the invention pertains to a surgical blade dispenser for storing a plurality of sharpened surgical blades.

In still another aspect, the invention concerns a surgical blade dispenser for storing a plurality of pre-sterilized surgical blades until ready for use and maintaining them in individually sterile condition until each is withdrawn from the dispenser.

In a further aspect, the invention concerns a dispenser for surgical blades which is adapted to permit an individual blade to be attached to a scalpel handle without manual handling of the blade by the surgeon or surgical assistant, thereby insuring that the blade can be lockingly engaged with the scalpel handle with complete safety and without contaminating the blade with germs or bacteria.

At present, disposable surgical scalpel blades are commercially available in several sizes, produced by various manufacturers. They can be obtained commercially in sterile or non-sterile packaging. These blades are adapted to fit conventional metal scalpel handles of various sizes to form knives used for a variety of purposes in hospitals (surgery, pathology laboratories, etc.), in research laboratories and in science departments at various schools and universities.

The typical commercially available surgical blade has a sharpened tip and cutting edge portion and a shank portion extending rearwardly therefrom. The shank portion of the blade is provided with an elongate aperture which is shaped and adapted to receive a mating elongate boss formed on the forward or attaching tip of a scalpel handle.

The elongate handle-engaging aperture of the blade has a widened rear portion and a narrowed forward portion. The widened rear portion of the aperture initially receives the engaging boss of the scalpel handle and guides the boss forward into the narrowed forward portion of the aperture. The boss is undercut such that the edges of the narrowed forward portion of the aperture are engaged between the scalpel handle and the undercut surface of the boss. When the boss is completely inserted within the blade aperture, the rear edge of the blade aperture snaps under the undercut surface at the rear of the engaging boss, thus achieving locking engagement between the blade and the scalepl handle.

To remove the blade from the scalpel handle, the rear edge of the blade is lifted away from the handle to disengage the rear end of the blade aperture from the rear end of the boss. The blade is then pushed forward until the undercut boss clears the narrowed forward portion of the blade aperture, permitting the blade to be lifted completely clear of the handle.

According to present practice, the above-described manipulative steps are performed by hand. This presents at least two problems, namely, the possibility that the very sharp cutting edge of the blade will contact and cut the fingers of the person performing the operation and, secondly, the blade may be contaminated by germs or bacteria carried on the manipulator's hands.

It would be highly desirable to provide a dispenser for surgical blades which would permit the blade to be completely engaged with the handle without touching the blade so as to avoid possible safety or contamination problems. It would further be desirable to confine the blade within a suitable enclosure which cna be conveniently held in one's hand during the blade attaching operation to avoid the above-described problems.

It would also be highly desirable to provide means for disengaging the blade from the scalpel handle without touching the blade and to provide means for storing the used blades so that they do not present a further safety hazard and for possible resharpening, sterilization and reuse.

Accordingly, it is a principal object of the present invention to provide a dispenser for surgical blades.

Still another object of the invention is to provide a surgical blade dispenser for holding at least one, preferably a plurality of surgical blades, and for dispensing them individually just prior to use thereof.

Still another object of the invention is to provide a surgical blade dispenser for storing and individually dispensing pre-sterilized surgical blades.

A still further object of the invention is to provide a surgical blade dispenser of the type described above, specially adapted to permit the blade to be attached to a scalpel handle while confined within the dispenser, so as to avoid the necessity or possibilty of the blade cutting the manipulator's hands or being contaminated by germs or bacteria carried by the hands.

A still further object of the invention is to provide a surgical blade dispenser having an integral blade disposal section, adapted to permit the used blade to be disengaged from the scalpel handle without manually contacting the blade and which provides convenient means for storing the used blades to avoid safety hazards and for possible resharpening, sterilization and reuse.

These and other, further and more specific objects and advantages of the invention will be apparent to those skilled in the art from the following detailed description thereof, taken in conjunction with the drawings, in which:

FIGS. 4A-4D and FIGS. 5A-5D are sectional views illustrating the steps involved in attaching a surgical blade contained within the dispenser of FIG. 1 to a conventional scalpel handle as illustrated in FIG. 2;

FIG. 4E is a sectional view showing the removal of the blade after attachment to the handle;

FIGS. 6A-6B are sectional views of the dispenser of FIG. 1, taken along section line 6—6 thereof, showing the means including a metal insert and the method of detaching the surgical blade from the scalpel handle in the disposal portion of the blade dispenser of FIG. 1; and FIG. 7 is a perspective view showing in greater detail the metal insert using in the disposal section of FIGS. 6A-6B.

Briefly, in accordance with my invention, I provide a surgical blade dispenser for holding at least one surgical blade until ready for use and for dispensing and attaching the blade to a conventional scalpel handle.

The conventional scalpel handle includes an elongate handle portion terminating at its forward end in a narrowed extension forming a blade attaching tip, having an elongate boss formed thereon.

The conventional surgical blade dispensed in accordance with the invention has a sharpened forward tip and cutting edge portion extending rearwardly therefrom along one side thereof and a shank portion extending rearwardly from the tip. The shank portion of the blade has an elongate aperture therein shaped and adapted to receive and lockingly engage with the mating elongate boss carried by the attaching tip of the scalpel handle.

The dispenser of the present invention comprises enclosure means defining a box for storing at least one of the surgical blades. The blade is positioned within the box by blade-positioning means for frictionally engaging the tip and at least a portion of the cutting edge of the blade and for supporting the rear edge of the shank portion of the blade in such fashion that the blade is slightly curvingly deformed from the rear end to the forward end thereof. A wall of the box proximate the shank end of the blade is provided with an aperture sized and shaped to receive the attaching tip of the scalpel therethrough a distance sufficient that the boss of the attaching tip can be inserted and lockingly engaged with the aperture in the shank portion of the blade.

In the preferred embodiment of the invention, the surgical blade dispenser described above includes means defining a used blade storage receptacle. The receptacle has an aperture in a wall thereof shaped and dimensioned to receive a scalpel handle tip therethrough with the surgical blade attached to it. The aperture has an edge thereof shaped to engage the shank end of the surgical blade and separated from the scalpel handle when the scalpel handle is withdrawn from the aperture, to detach the blade from the handle and retain it within the disposal receptacle.

Figure 1:
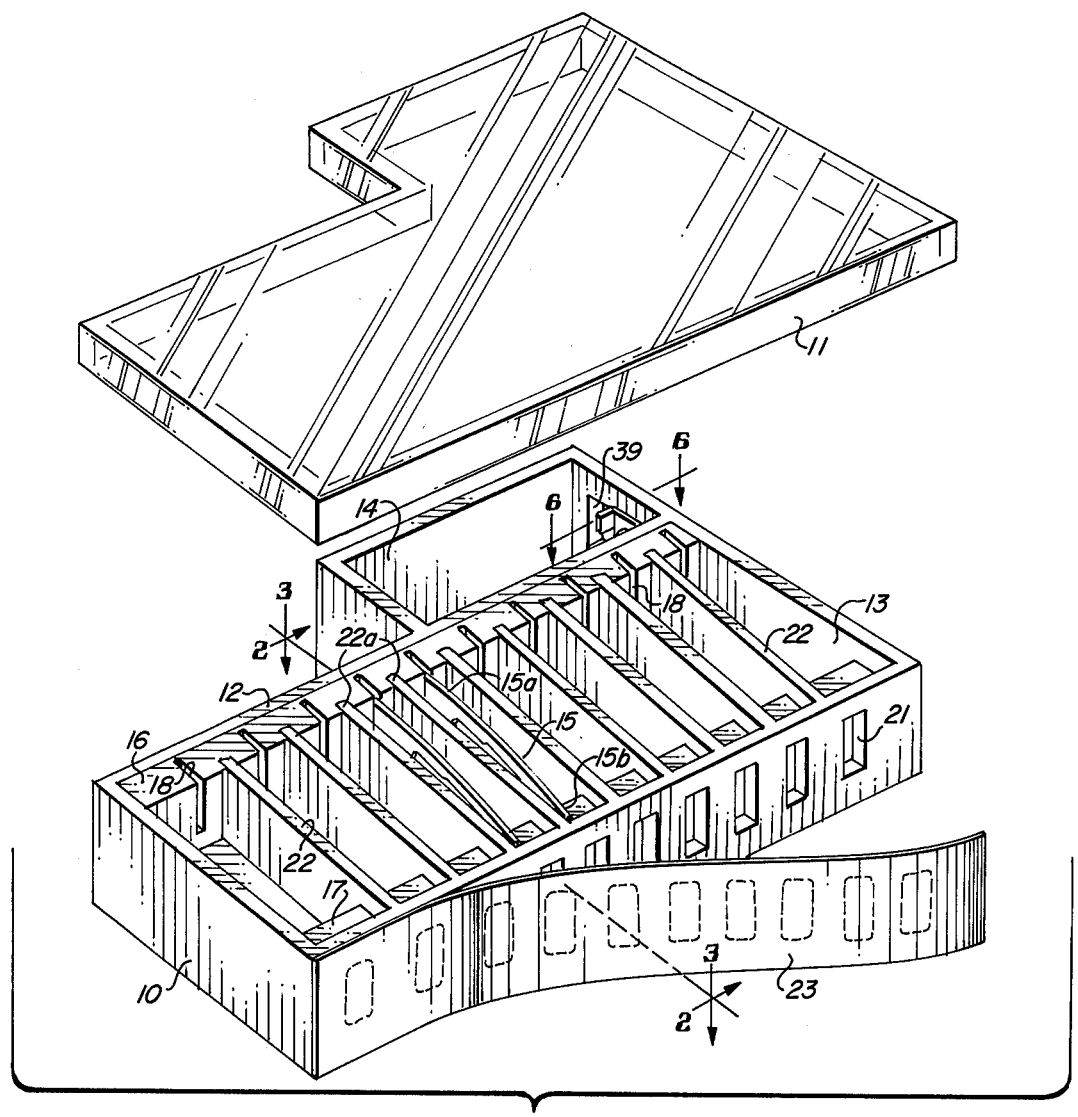
FIG. 1 is an exploded perspective view of a surgical blade dispenser embodying the principles of the present invention.
Figures 2, 3:
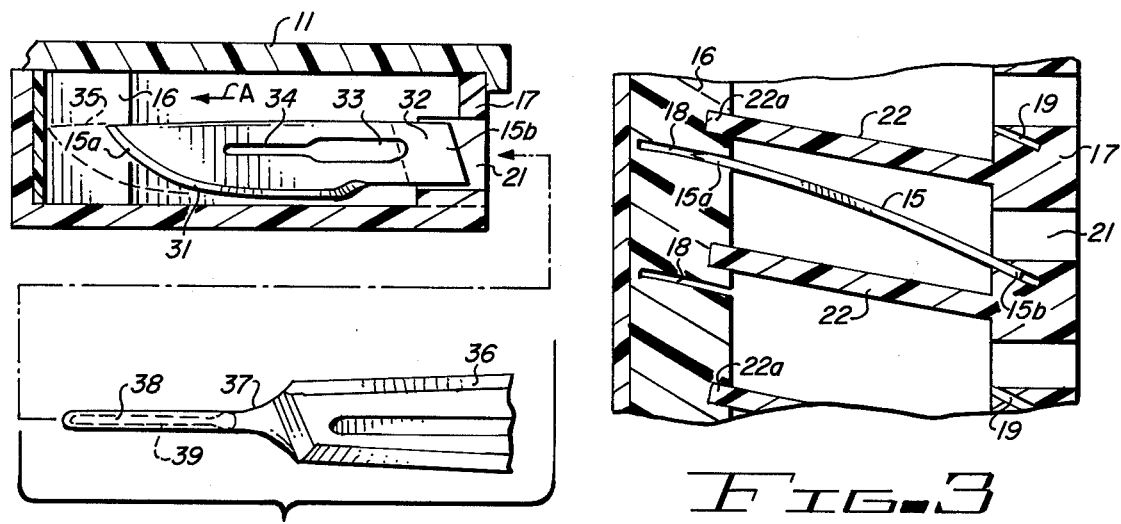
FIG. 2 is a partial sectional view of the dispenser of FIG. 1, taken along section line 2—2 thereof, illustrating the position in which surgical blades are disposed within the dispenser prior to use and further illustrating the forward end of a conventional scalpel handle to which the blades are later attached, as described below.
FIG. 3 is a sectional view of the dispenser of FIG. 1, taken along section line 3—3 thereof, showing further details of the manner in which the blades are positioned within the dispenser before use.

Turning now to the drawings, FIGS. 1-3 illustrate the blade dispenser of the invention which comprises a box 10 formed of plastic, metal or other suitable material, having a cover 11. The cover 11 is separately formed and attached to the box 10 after the dispenser is loaded with blades, as described below. The cover 11 may be permanently secured to the box 10 or may be detachably secured thereto, according to the presently preferred embodiment of the invention.

The box 10 is generally divided by the rear wall thereof 12 into two separate compartments, a blade storage and dispensing compartment 13 and a used blade removal and storage receptacle 14.

A plurality of surgical blades 15 are positioned within the storage and dispensing compartment 13 by means of a blade-positioning block 16 and slots formed in the forward wall 17 of the box 10. The block 16 which positions the forward ends 15a of the blades 15 is formed of a relatively soft plastic which will frictionally engage the forward ends 15a of the blades 15 without dulling the cutting edge formed on the tip and underside thereof.

The forward ends 15a of the blades 15 are frictionally engaged with the block 16 in slots 18 formed therein. The rear ends 15b of the blades 15 are received and held within angularly disposed slots 19 formed in the forward wall of the box 10. The slots 19 and their respective mating slots 18 are offset in such fashion that the blade 15 is slightly deformed so as to curve laterally as shown away from apertures 21 formed in the front wall 17 of the box 10. The purpose for deforming the blade so as to curve, as shown, will be explained below.

If desired, each of the blades 15 in the storage and dispensing compartment 13 can be separated by partitions 22 formed integrally with the front wall 17 of the box 10 and extending to and received within notches 22a formed in the blade-positioning block 16. A piece of adhesive-backed puncturable tape 23 formed of thin metal foil, plastic or the like, can be used to seal the openings 21 in the box 10. The partitions 22 and the puncturable tape 23 cooperate to maintain each of the blades 15 in a separate compartment, sealed from the ambient atmosphere until ready for use. In this manner, pre-sterilized blades can be maintained in a completely sterile environment until the puncture tape sealing the aperture 21 leading to the compartment in which the blade 15 is stored is broken by insertion of the scalpel handle.

The method of attaching a blade to the scalpel handle and withdrawing it from the dispenser will now be described. Referring first to FIG. 2, the surgical blade is formed of thin, high-quality metal and includes a sharpened tip and cutting edge portion 31 extending rearwardly from the forward end 15a of the blade. A shank portion 32 extends rearwardly from the tip 15a and sharpened cutting edge 31 of the blade. The blade is provided with an elongate aperture 33 which is wider at the rear end thereof and which converges to a narrowed forward portion 34. As the blade is held in the dispenser, the tip portion 15a thereof is received and frictionally engaged in the blade-positioning block 16 in such manner that force exerted on the blade in the direction of the arrow A can cause the blade to move forward in its slot 18 to the position shown by the dashed lines 35, at which point the rear end 15b of the shank portion of the blade will just clear the slot 19 formed in the front wall 17 of the box 10.

The forward end of a conventional scalpel handle is also illustrated in FIG. 2. The handle portion 36 of the scalpel handle terminates at its forward end in a narrowed extension 37 forming a blade-attaching tip. The tip has an elongate boss 38 formed thereon which is undercut as shown by the dashed lines 39.

Referring now to FIGS. 4A-4D and 5A-5D, as the scalpel blade handle 36 is inserted in the direction of the arrow B through one of the openings 21 in the forward wall 17 of the box 10, the forward end of the boss 38 contacts the curvingly extending blade 15 and is received within the wider portion 33 of the slot formed in the blade 15, all as shown in FIGS. 4A and 5A. As shown in FIGS. 4B and 5B, further movement of the scalpel handle 36 in the direction of the arrow B causes the boss 38 to move forward into the narrowed portion 34 of the aperture in the blade 15, at which point the blade 15 is held between the tip portion 37 of the scalpel handle 36 and the undercut side of the boss 38. The rear end of the boss 38 has not yet cleared the rear end of the aperture 33.

Still further movement of the handle 36 in the direction of the arrow B, as shown in FIGS. 4C and 5C, causes the rear end of the boss 38 to clear the rear edge 33 of the slot in the blade 15, all the while causing the forward end 15a of the blade 15 to move further into the blade retaining slots 18 formed in the blade-positioning block 16, bringing the rear edge 15b of the blade 15 just clear of the slot 19 formed in the front wall 17 of the box portion of the dispenser. At this point, as shown in FIGS. 4D and 5D, the rear end 15b of the blade 15 is free to snap arcuately in the direction of the arrow C toward the blade-engaging tip 37 of the handle 36, at which point the rear end of the slot 33 snaps over the rear end of the boss 38 completing engagement of the blade 15 with the handle 36.

The assembled blade 15/handle 36 combination is then withdrawn through the aperture 21 in the direction of the arrow D, as an integral ssembly.

Removal of the blade from the scalpel handle is illustrated in FIGS. 6A, 6B and 7. The blade 15 attached to the tip portion 37 of the handle 36 is inserted within an aperture 39 in a wall of the used blade storage receptacle 6. One edge of the aperture 39 is provided with a metal insert 41 having outwardly projecting ears 42 which slip under the rear end 15b of the blade 15. When the handle 36 is moved laterally in the direction of the arrow C, the rear edge 15b of the blade 15 is separated from the rear end of the boss 38 such that the handle 36 can then be withdrawn through the aperture 39 in the direction of the arrow D, leaving the blade 15 within the used blade storage receptacle 6.

As will be observed by those skilled in the art, the dispenser herein disclosed provides a quick, positive, safe and sanitary method of storing, attaching and detaching surgical blades from scalpel handles, to overcome the problems described above associated with manually attaching and detaching surgical blades from scalpel handles.

Having described my invention in such clear, concise and exact terms as to enable those skilled in the art to understand and practice it, and having described the presently preferred embodiment thereof, I claim:

1. A surgical blade dispenser for holding at least one surgical blade until ready for use, and for dispensing and attaching said blade to a scalpel handle,
   said scalpel handle including an elongate handle portion terminating at its forward end in a narrowed extension forming a blade attaching tip, said tip having an elongate boss carried thereon,
   said surgical blade having a sharpened tip and cutting edge portion and a shank portion extending rearwardly therefrom, the shank portion of said blade having an elongate aperture therein shaped and adapted to receive and lockingly engage with said mating elongate boss carried by the attaching tip of said scalpel handle,
   said dispenser comprising:
   (a) enclosure means defining a box for storing at least one of said surgical blades;
   (b) blade positioning means within siad box for frictionally engaging
     (i) the tip and at least a portion of the cutting edge of said blade, and
     (ii) the shank portion of said blade to position said blade such that the shank portion of said blade curvingly extends toward a wall of said box proximate the shank portion of said blade, said wall having at least one aperture therein sized and shaped to receive the attaching tip of said scalpel handle therethrough, a distance sufficient that the boss of said attaching tip can be inserted and lockingly engaged with the aperture in the shank portion of said blade.

2. Surgical blade dispenser of claim 1 including means defining a used-blade storage receptacle carried by said box, said receptacle having an aperture in a wall thereof shaped and dimensioned to receive therethrough a scalpel handle tip and surgical blade attached thereto, said aperture having an edge thereof shaped to engage the shank end of said surgical blade and separate it from the scalpel handle when said scalpel handle is withdrawn, to detach said blade from said handle and retain said blade in said disposal receptacle.

* * * * *